(12) United States Patent
Parks et al.

(10) Patent No.: US 8,211,107 B2
(45) Date of Patent: Jul. 3, 2012

(54) MODULAR, BLADE-ROD, INTRAMEDULLARY FIXATION DEVICE

(75) Inventors: Brent G. Parks, West Friendship, MD (US); Christopher Chiodo, Walpole, MA (US); Lew C. Schon, Baltimore, MD (US)

(73) Assignee: Concepts In Medicine, LLC, West Friendship, MD (US)

( * ) Notice: Subject to any disclaimer, the term of this patent is extended or adjusted under 35 U.S.C. 154(b) by 769 days.

(21) Appl. No.: 11/801,542

(22) Filed: May 10, 2007

(65) Prior Publication Data

US 2009/0062796 A1    Mar. 5, 2009

Related U.S. Application Data

(60) Provisional application No. 60/799,222, filed on May 10, 2006.

(51) Int. Cl.
*A61B 17/78* (2006.01)
(52) U.S. Cl. .......................................................... 606/64
(58) Field of Classification Search .............. 606/62–68, 606/96, 86 R, 104
See application file for complete search history.

(56) References Cited

U.S. PATENT DOCUMENTS

| | | | | |
|---|---|---|---|---|
| 2,985,168 | A * | 5/1961 | Salo Jonas et al. | 606/96 |
| 4,103,683 | A * | 8/1978 | Neufeld | 606/67 |
| 4,522,202 | A * | 6/1985 | Otte et al. | 606/62 |
| 4,697,585 | A * | 10/1987 | Williams | 606/64 |
| 4,946,459 | A * | 8/1990 | Bradshaw et al. | 606/62 |
| 4,978,349 | A * | 12/1990 | Frigg | 606/67 |
| 5,002,545 | A * | 3/1991 | Whiteside et al. | 606/80 |
| 5,178,621 | A * | 1/1993 | Cook et al. | 606/96 |
| 5,190,547 | A | 3/1993 | Barber | 606/79 |
| 5,346,496 | A * | 9/1994 | Pennig | 606/96 |
| 5,352,228 | A * | 10/1994 | Kummer et al. | 606/64 |
| 5,391,169 | A * | 2/1995 | McGuire | 606/79 |
| 5,474,561 | A * | 12/1995 | Yao | 606/98 |
| 5,478,341 | A * | 12/1995 | Cook et al. | 606/62 |
| 5,499,985 | A * | 3/1996 | Hein et al. | 606/99 |
| 5,540,692 | A | 7/1996 | Tidwell | 606/79 |
| 5,649,928 | A | 7/1997 | Grundel | 606/88 |
| 5,681,320 | A | 10/1997 | McGuire | 606/104 |
| 5,749,875 | A * | 5/1998 | Puddu | 606/87 |
| 5,766,259 | A | 6/1998 | Sammarco | 623/21 |
| 5,810,822 | A * | 9/1998 | Mortier | 606/86 B |
| 5,993,453 | A | 11/1999 | Bullara | 606/79 |
| 6,039,739 | A * | 3/2000 | Simon | 606/64 |
| 6,205,411 | B1 | 3/2001 | DiGioia et al. | 703/11 |
| 6,224,601 | B1 * | 5/2001 | Friedl | 606/64 |

(Continued)

*Primary Examiner* — Eduardo C Robert
*Assistant Examiner* — Jerry Cumberledge
(74) *Attorney, Agent, or Firm* — Larry J. Guffey

(57) ABSTRACT

The intramedullary fixation device for use in fixing the relative position between a tubular bone and an adjoining bone has, according to the present invention, an intramedullary nail that is inserted into the medullary canal of the tubular bone whose position is to be fixed, an elongated blade for insertion into the adjoining bone whose position is to be fixed relative to that of the tubular bone, a coupling element for fixing and locking the relative position of the nail and blade after their insertion, and a means for locating and positioning within the bones to-be-treated the nail and blade. Furthermore, the blade has a cross-sectional shape that is configured in consideration of the geometry of the bone into which the blade is to-be-placed and so as to enhance the ability of the blade to stabilize the bone, and these elements are configured so that they do not have to be decouple during the process of inserting the nail and blade.

7 Claims, 14 Drawing Sheets

U.S. PATENT DOCUMENTS

| | | |
|---|---|---|
| 6,228,089 B1 | 5/2001 | Wahrburg ........................ 606/86 |
| 6,254,605 B1 | 7/2001 | Howell ............................ 606/96 |
| 6,267,762 B1 | 7/2001 | Millard ........................... 606/54 |
| 6,572,620 B1 | 6/2003 | Schon et al. .................... 606/62 |
| 6,579,293 B1 * | 6/2003 | Chandran ........................ 606/64 |
| 6,712,823 B2 * | 3/2004 | Grusin et al. ................... 606/87 |
| 7,867,231 B2 * | 1/2011 | Cole ................................ 606/64 |

\* cited by examiner

MODULAR, BLADE-ROD, INTRAMEDULLARY FIXATION DEVICE

CROSS-REFERENCE TO RELATED APPLICATION

This application claims the benefit of Provisional Patent Application No. 60/799,222, filed May 10, 2006 by the present inventors. The teachings of this application are incorporated herein by reference to the extent that they do not conflict with the teaching herein.

BACKGROUND OF THE INVENTION

1. Field of the Invention

This invention relates to improved internal fixation means used in surgical procedures to treat fractured bones, pending fractures of bones, non-unions, arthritis, as well as any other procedure in which an attempt is made to surgically fuse two or more bones. More particularly, this invention relates to an orthopedic surgical implant and its method of use for stabilizing the relative position between a bone having a medullary canal and an adjoining bone or bone section.

2. Description of the Related Art

In recent years, both solid and tubular, metal rods or intramedullary nails have gradually gained importance in orthopedic surgery. They have in many situations become the standard surgical implant for stabilizing fractures or pending fractures in large tubular bones, such as the femur (thigh bone), tibia (leg bone) or humerus (upper arm bone).

The shape and configuration of such intramedullary nails has been a topic of much inventive effort. From initially circular or almost circular cross-sections, these nails have, in order to minimize the damage done to the bone during their placement in the body, come to be designed such that their cross-sections correspond to the anatomy of the medullary canals in which they are to be used.

For example, for the humerus bone, in which the medullary canal is not round along its entire length but is in fact flat and thin in the distal part, a nail with a flattened cross-section for its distal end has been developed. See U.S. Pat. No. 6,231,576.

In order to avoid the rotation of bone fragments and their shortening in multifragmented fractures, these nails have come to be used with various accessories, such as anchoring screws and other elongated, blade-like elements, that pass through holes in such nails and attach to the various bone fragments. See U.S. Pat. Nos. 5,928,235, 6,077,264, 6,235,031 and 5,562,667 for examples of such elements and their methods of use for stabilizing fractures of the neck of the femur.

Despite the extensive development of such intramedullary nails and accessories, it was recognized that they continued to exhibit certain disadvantages. For example, their designs were such that: (1) they often offered only minimal flexibility in addressing situations in which the bones or bone fragments to be stabilized have unique geometries or orientations, (2) they often involved relatively complex designs which tended to increase their costs of manufacture, and (3) their uses were confined primarily to the treatment of fractures and pending fractures in individual large, tubular bones and for limited fusions of the ankle and knee—they had also been used in situations to stabilize one or several bones, but (4) they did not provide stability in all three, orthogonal planes of motion.

In an attempt to address these disadvantages, the modular, blade-rod intramedullary fixation device of U.S. Pat. No. 6,572,620 was developed by the present inventors. See FIGS. 1-3.

FIG. 1 depicts the situation in which this intramedullary fixation device is being used to stabilize the position of the shin bone (tibia) relative to the adjoining ankle (talus) and heel (calcaneus) bones. The device is seen to consist of an intramedullary nail or rod that has been inserted through the bottom of the foot and into the medullary canal of the tibia. A threaded bore extends from the nail's proximate end and along a specified portion of its longitudinal axis. See FIG. 2.

An elongated blade is seen to have been driven through the adjoining ankle bone whose position is to be fixed relative to that of the tibia. A passageway adjacent the blade's proximate end extends between its top and bottom surfaces, thereby providing a passage through which a screw may be passed in order to lock the blade and nail together. When the nail's design is such that its proximate end section is not perpendicular to its longitudinal axis, a washer is used to align the longitudinal axes of the nail and the screw.

FIG. 3 provides a perspective view of an insertion jig or alignment apparatus that is used to locate and precisely position, within the bones to-be-treated, the nail and blade of this device. It consists of a base portion with a seat section upon which the to-be-inserted nail and washer may be aligned and positioned prior to insertion. It also includes a detachable, blade alignment section that has an orifice through which the blade is passed for insertion into the targeted bone. Into this orifice can also be inserted a guidewire adapter which contains an orifice in which a guide pin can be placed and then fed into the precise position where the blade is to-be-inserted into the bone. The alignment apparatus also has a tower section in which are located additional holes which serve to locate and align with the openings that are situated along the length of the nail. These holes are used to help fasten additional support screws or other attachment means for providing further stabilization means for the nail.

Despite improving upon the prior technology, it has been recognized that the intramedullary fixation device of U.S. Pat. No. 6,572,620 still has certain drawbacks. For example, it can encounter situations in which the shapes of the bones, whose positions it is meant to stabilize, make insertion of the intramedullary rod and blade exceedingly challenging.

This situation is due, in part, to the need to partially or completely detach the insertion jig from the rod so as to make room beneath the rod to allow the blade to pass below the rod. This introduces the potential for instability between the bones and for loss of alignment of the blade relative to the rod, loss of alignment of the rod relative to the foot, and loss of alignment of those bones held by the rod and the blade. Additional efforts to stabilize the bones without the use of the jig can necessitate other procedural steps that result in increased surgical trauma for the patient.

Thus, there still exists a continuing need for the development of new and improved intramedullary fixation devices.

3. Objects and Advantages

Recognizing the need for the development of improved internal fixation means that are used in surgical procedures to treat fractured bones, etc., the present invention is generally directed to satisfying the needs set forth above and overcoming the disadvantages identified with prior art devices.

It is an object of the present invention to provide an improved intramedullary fixation device and method that offers maximum flexibility in addressing situations in which the bones or bone fragments to be stabilized have unique geometries or orientations.

It is another object of the present invention to provide an improved intramedullary fixation device that can be used without having to decouple its component parts during their surgical insertion; thereby preventing the possibility that the bones which have been aligned for fixation might fall out of alignment.

It is yet another object of the present invention to provide an improved intramedullary fixation device and method that can be used for treating situations other than just the treatment of fractures and pending fractures in individual large, tubular bones. For example, to treat the situation in which the position of two or more adjoining bones are stabilized in order to allow and promote surgical fusion, or arthrodesis, of these bones. Some examples of such non-fracture, clinical applications include arthritis, infection, neuropathy and deformity.

It is a further object of the present invention to provide a method and device for providing stabilization of the relative position between two or more bones that may or may not share adjacent surfaces (e.g., the tibia, talus and calcaneus).

It is a still further object of the present invention to provide a device and method that will advance the utility of intramedullary nails in orthopedic medicine.

These and other objects and advantages of the present invention will become readily apparent as the invention is better understood by reference to the accompanying drawings and the detailed description that follows.

SUMMARY OF THE INVENTION

Recognizing the need for the development of improved intramedullary fixation means, the present invention is generally directed to satisfying the needs set forth above and overcoming the disadvantages identified with prior art devices.

In accordance with one preferred embodiment of the present invention, the foregoing need can be satisfied by providing an intramedullary fixation device for use in fixing the relative position between a bone having a medullary canal and an adjoining bone or section of bone. Such a device comprises: (1) an intramedullary nail that is to be inserted into the medullary canal of the tubular bone whose position is to be fixed, (2) an elongated blade for insertion into the adjoining bone whose position is to be fixed relative to that of the tubular bone, (3) a coupling element for fixing and locking the relative position of the nail and blade after their insertion, and (4) a means for locating and positioning within the bones to-be-treated the nail and blade. Furthermore, the blade has a cross-sectional shape that is configured in consideration of the geometry of the bone into which the blade is to-be-placed and so as to enhance the ability of the blade to stabilize the bone, and these elements are configured so that they do not have to be decouple during the process of inserting the nail and blade.

According to a second embodiment of the present invention, a method is provided for stabilizing a specified, relative position between a tubular bone having a medullary canal and an adjoining bone or section of bone. This method comprises the steps of providing the listed elements for the fixation device and then seating the intramedullary nail and blade in the respective tubular and adjoining bones, and utilizing the coupling means so as to lock the elements together and prevent relative movement between the treated bones.

DESCRIPTION OF THE PREFERRED EMBODIMENT

Figure 1:
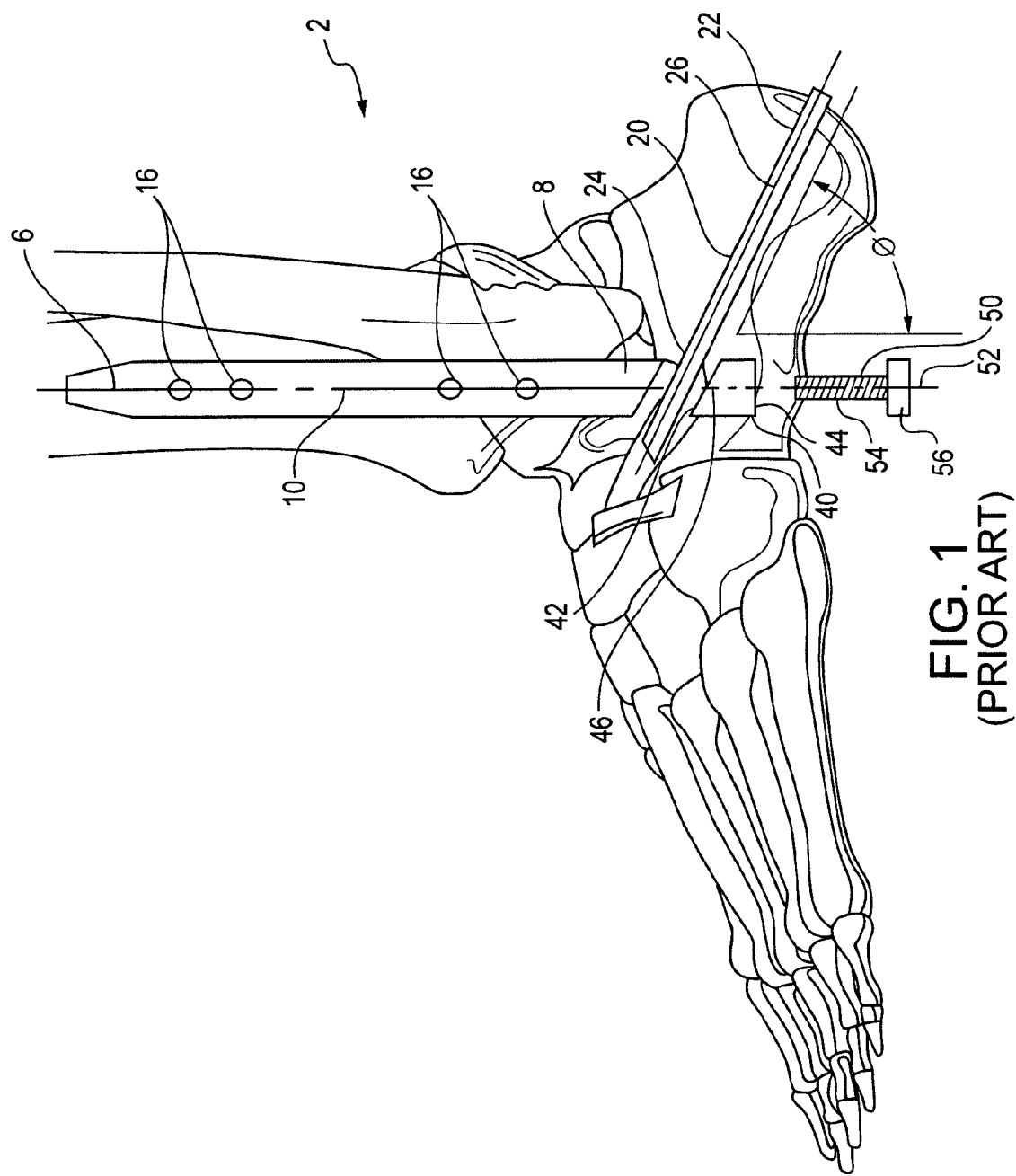
FIG. 1 is a plan view of the modular, blade-rod intramedullary fixation device of U.S. Pat. No. 6,572,620 when it is being used to stabilize the position of the shin bone (tibia) relative to the adjoining ankle bone (talus).
Figure 2:
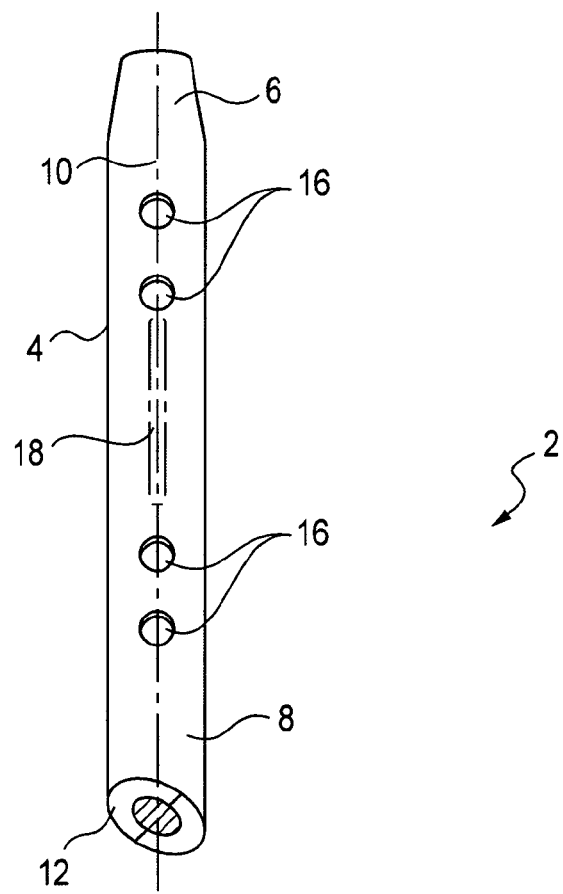
FIG. 2 is an exploded perspective view of the elements that comprise the device shown in FIG. 1.
Figure 2:
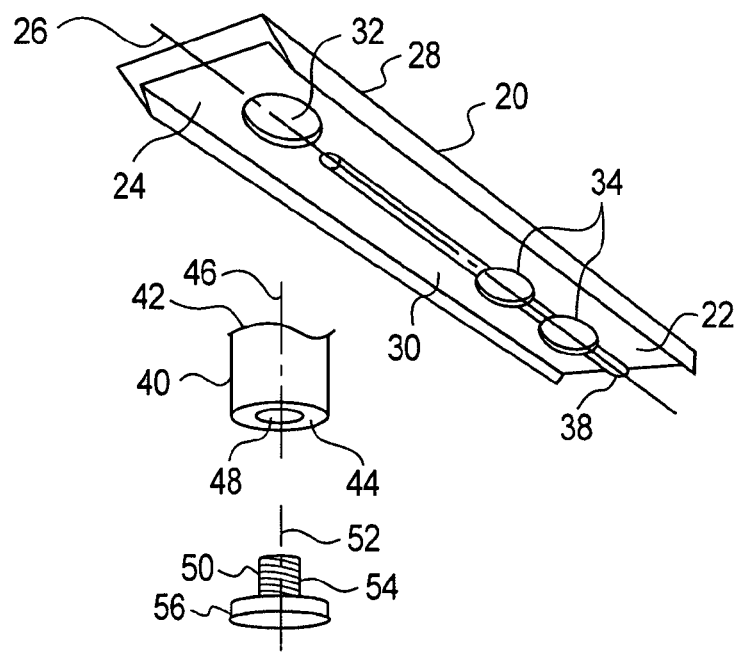

Before explaining at least one embodiment of the present invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

The present invention is used for the stabilization of fusions and or fractures of bodily bones and joints. To explain this invention, its use has been illustrated within in relation to an ankle surgery.

To better understand the present invention, it is instructive to consider the procedural steps that are involved in an ankle stabilization surgery which utilizes the previously discussed blade and nail/rod intramedullary fixation device of U.S. Pat. No. 6,572,620 and its alignment apparatus or insertion jig.

Prior to insertion of the rod, the joint surfaces to be fused are prepared in the standard fashion. This is typically performed through one or two skin incisions medially or laterally on the extremity but may also be performed through anterior and/or posterior skin incision(s). Alternatively, if a fracture is present, the fracture fragments are reduced and properly aligned if significant displacement is present. This reduction may be performed without an incision or through antererior, medial, lateral, or posterior incision(s).

Next, an incision is made at the intended location of the rod insertion. A guide wire is inserted through this incision and into the adjacent/involved bone under fluoroscopic guidance. The wire is then advanced through the bone or joint segments that require stabilization. This guide wire may then be changed to a more flexible wire with a bulbous end. A cannulated reaming may then be inserted over the guide wire and used to create an appropriately sized tunnel in the bone or joint segments that require stabilization. This tunnel accepts the rod. At this point, the reaming device is removed. If necessary, the guide wire may be changed for one with a smooth tip.

Figure 3:
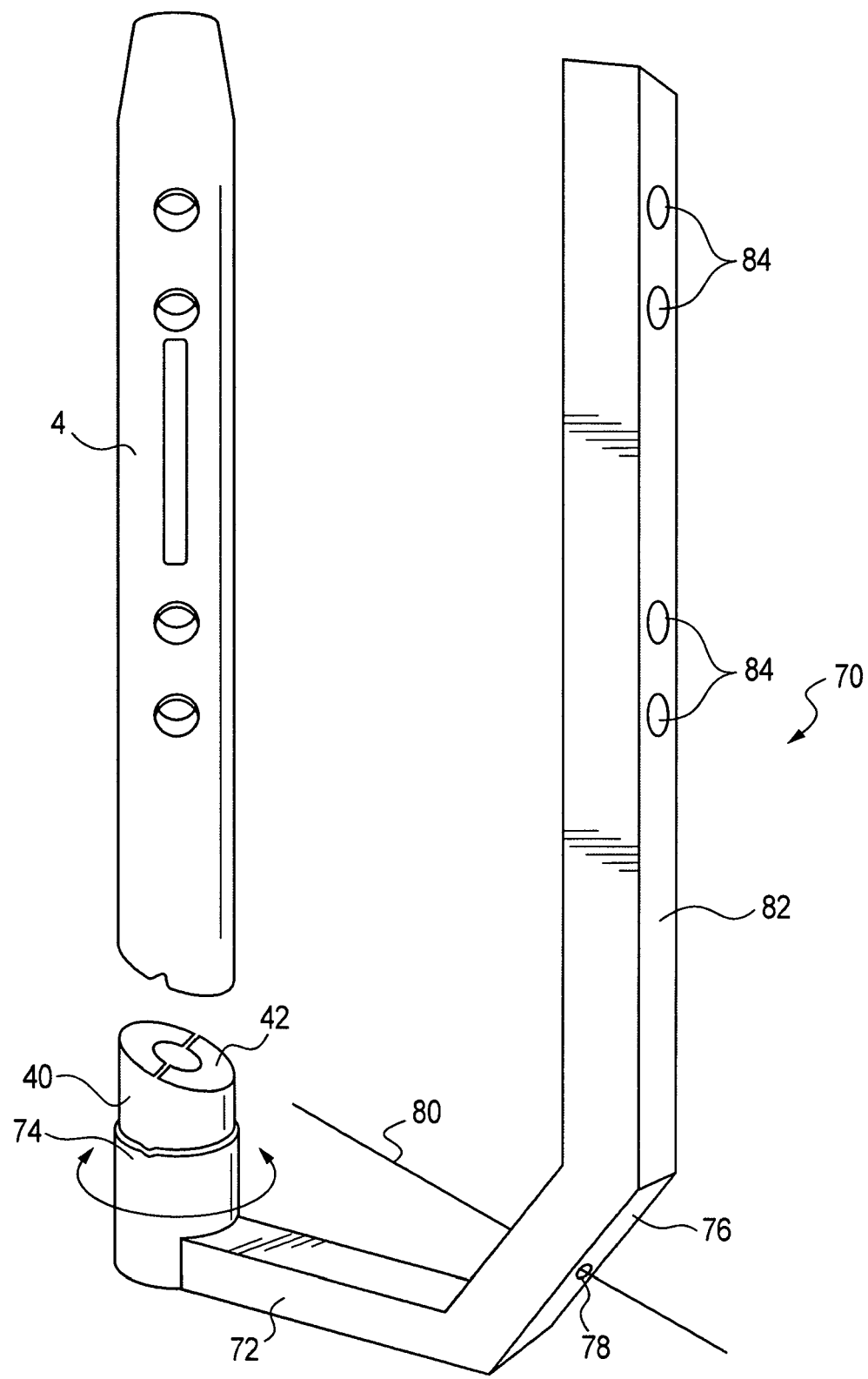
FIG. 3 is a perspective view of an alignment apparatus which is used to locate and precisely position, within the bones to-be-treated, the nail and blade of the intramedullary fixation device shown in FIG. 1.

Next, the rod is connected to the insertion jig device. The insertion jig is comprised of a base which has a seat section to which the rod can be connected. Also attached to this base is a tower section that is configured such that its centerline is parallel to that of the rod when it is attached to the jig's seat section. A detachable blade alignment is also connected to the seat section. See FIG. 3.

A rod is secured to the seat section and inserted from distal to proximal, or proximal to distal, through the bone or joint segments that require stabilization. The tower section of the jig is positioned parallel to the appropriate axis of the extremity. Proper position of the rod/jig construct is determined and confirmed by x-ray or fluoroscopy.

The advanced end (furthest from the entry point) of the rod is secured to the bone using one or two screws. These are inserted by drilling perpendicular to the rod's centerline and through the surrounding bone using corresponding alignment or drill holes in the jig's tower section.

Next, using the jig's detachable blade alignment section, and in preparation for a blade's insertion, one or more guide wires are inserted into the terminal bone or bone segment. The blade alignment section contains a detachable adapter that has an orifice through which a guide wire can be fed at a prescribed angle to the rod's centerline. This guide wire is advanced to a point beneath or through a slot in the trailing end of the rod. For this step of the procedure, the jig may be rotated as needed.

A cannulated blade is then inserted and driven over the wire(s) into the terminal bone or bone segment. The depth to which the blade is driven may be guided by a pivoting bushing on the blade alignment section of the jig. When this bushing is rotated upwards it serves as a stop such that the leading edge of the blade is inserted to an appropriate pre-determined depth. When the bushing is rotated down, the blade is further inserted.

As previously mentioned, at some point in this insertion the jig will have to be decoupled from the rod so that its seat portion can be moved away from the rod's trailing end to make room for the blade to pass beneath the rod.

Once the blade is fully inserted to the appropriate depth, the blade is secured to the rod. This is accomplished by a screw that is inserted into the trailing end of the rod. This screw passes through a hole, slot, or recess in the blade, and thereby secures and compresses the blade to the rod.

The relative angulation between the blade and the rod may or may not require the use of an angled washer. The addition of an angled washer allows insertion and positioning of the blade in the terminal bone or bone segment at an angle other than a 1190-degree right-angle to the rod.

As previously mentioned, recognizing the alignment problems that can occur when this jig is disconnected from the rod to allow the blade to slip beneath the rod, we set about the task of developing improvements to our prior blade-rod system which would not require this step of decoupling the rod from its insertion jig. Our improved blade and nail/rod intramedullary fixation devices, including their insertion jigs, are disclosed below.

Figure 4:
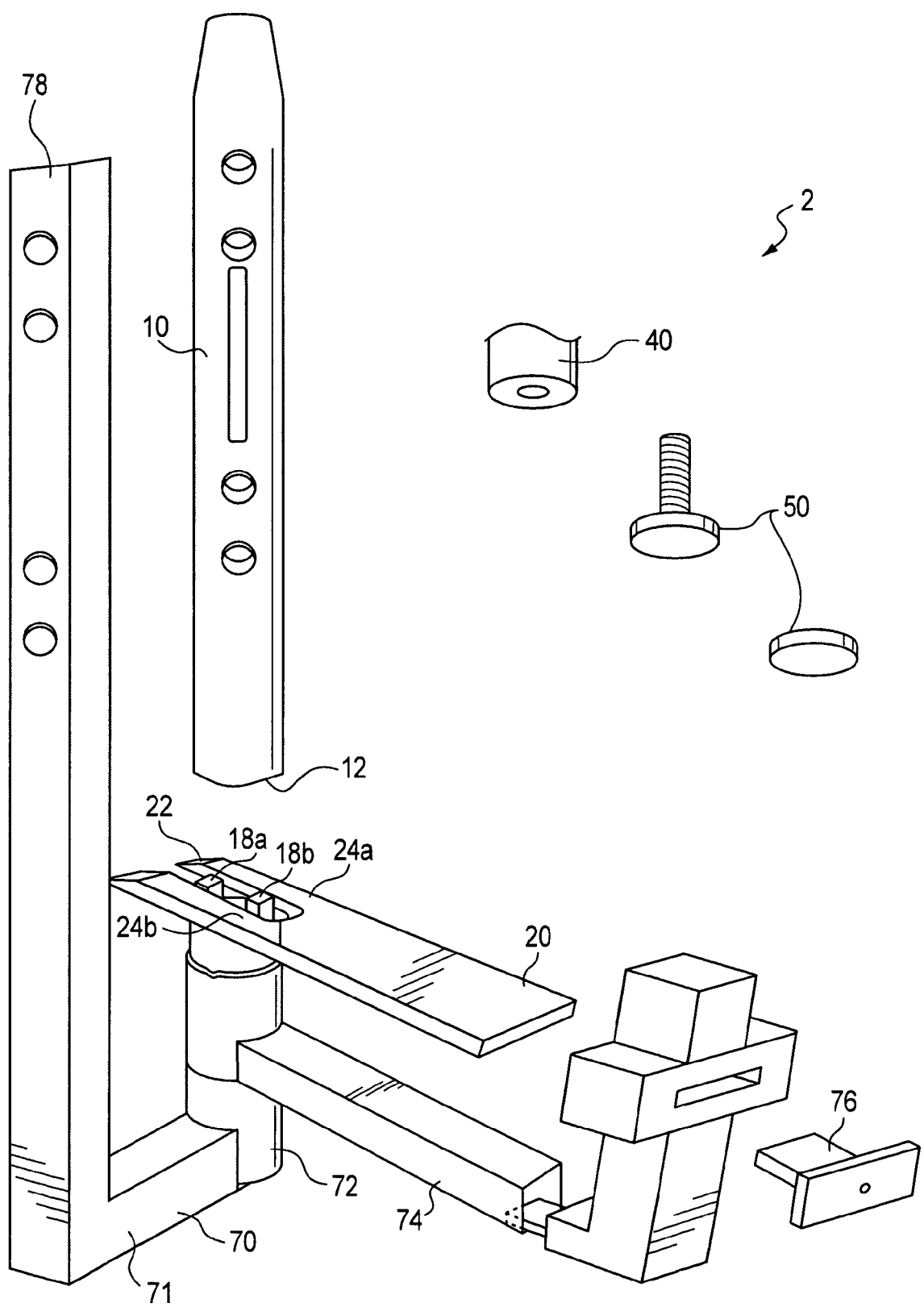
FIG. 4 is a perspective view of a preferred embodiment of the present invention.

FIG. 4 shows a first preferred embodiment of such an improved device 2. It consists of a rod or nail 10, a blade 20, a screw or coupling element or locking/end cap 50, and an insertion jig 70 or means for locating and positioning within the bones to-be-treated the nail and blade. When the angle between the blade and rod's centerlines is not perpendicular, a sloped washer 40 may also be used.

As before, the insertion jig consists of a base 71, a seat section 72, a detachable, blade alignment section 74, a guidewire adapter 76, and a tower section 78.

In this embodiment, the blade has distal and proximate ends with a longitudinal axis extending between these ends. It has a cross-sectional shape and a surface area that is configured and chosen in consideration of the geometry of the bone into which it is to-be-placed and so as to enhance the blade's ability to adhere to and stabilize the bone (even though the bone or bone fragments may have a unique geometry and require stabilization in any one of a wide range of orientations) while also allowing easy passage of the blade through the bone. In FIG. 4, the blade's proximate end has a leading or cutting edge 22 which is configured so as to enable the blade to be inserted without requiring the parts of the fixation device to be decoupled during insertion of the nail and blade—it's leading edge has a gap or recess in the form of two prongs 24a, 24b (for example, a fork-like construct). The prongs taper to a sharpened edge to allow penetration and impaction of the blade into a targeted bone.

Figure 5:
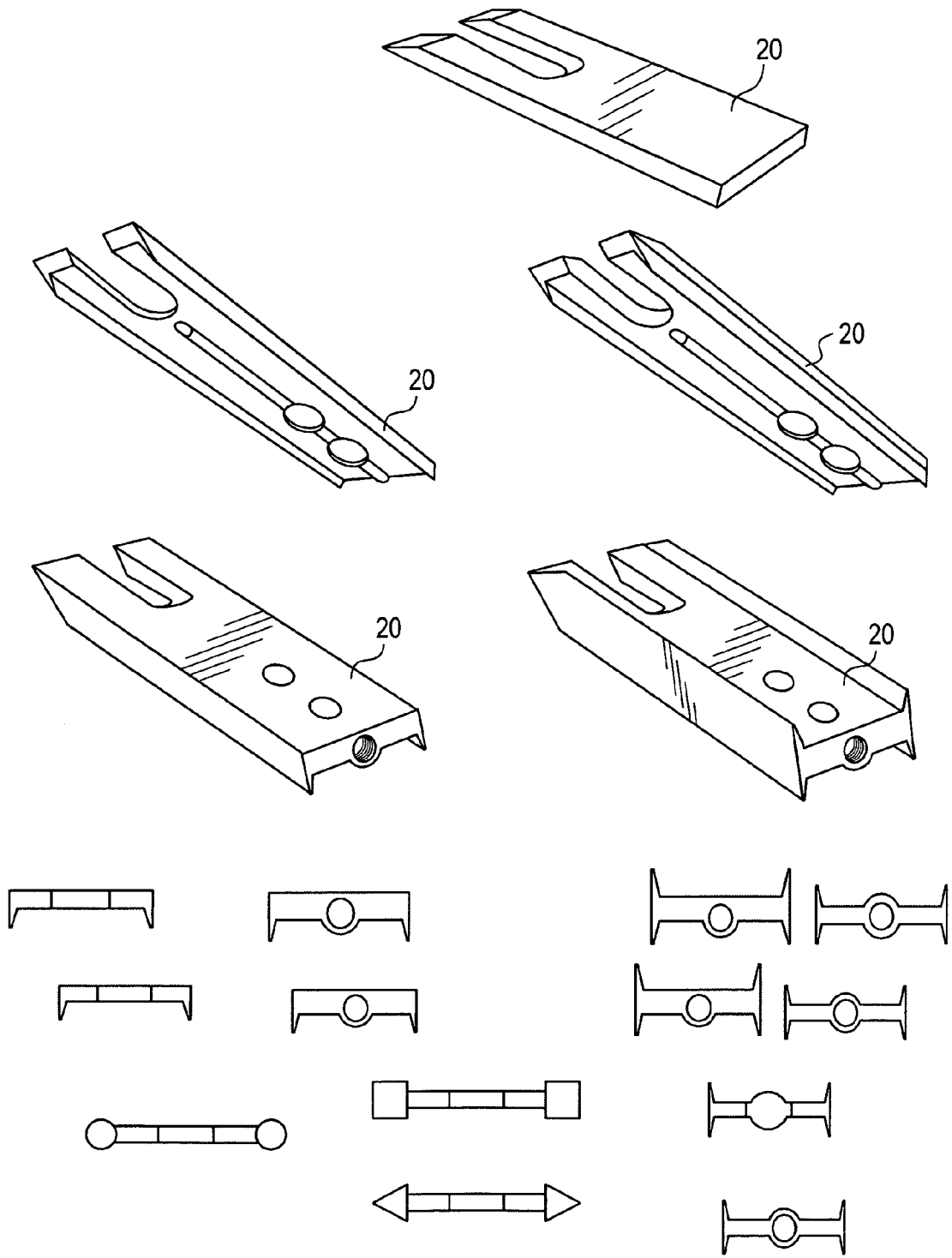
FIG. 5 shows some of the many alternative configurations and cross-sectional shapes that can be used with the blade of the present invention.

As shown in FIG. 5, the configuration and cross-sectional shapes of such a blade can take many configurations. For example, the prongs may have rails or I-beam configurations, and may be rectangular, circular, tubular, triangular, conical, stellar, trapezoidal or other suitable shape. One or several rails can be oriented perpendicular to blade, and be rectangular, circular, tubular, triangular, conical, stellar, star, triangular, trapezoidal or other suitable shape. Such rails may also be partially or completely tapered, either on the leading edge or over the entirety of the blade. The rails may be on one or both sides of the blade.

The width of these prongs must be such as to maintain a surface area on both sides of the guide wire that is sufficient to act as a mating surface between the rod and the locking cap 50 that is used to lock the blade to the rod. The blade can be as wide as the rod, or less wide, or wider than the blade. The distance between the extensions must be such that it accommodates the connection means of the locking cap.

With the prong-ended blade of the present invention, several methods are available for modifying the device so that it is not necessary to disconnect the jig from the rod during the middle of a surgical procedure. These include: (a) downsize or undersize the jig's seat 72 at its connection points to the rod enough to allow passage of the blade's prongs on either side of the rod. This can be accomplished with a taper or severe decrease in the diameter of the jig's seat at its connection point with the rod; (b) maintain the diameter of the jig's seat, but provide it with one or more fixed or mobile protrusions 80a, 80b that allow passage of the blade's prongs around these protrusions.

If two protrusions are used, the one that first encounters the advancing edge of the blade (the near one) can be made removable (e.g., retractable (moved by a screw mechanism, or other sliding mechanism), cuttable or meltable (some material that can dissolve or melt)). Additionally, some removable filler, that cuts or melts easily, may be placed to temporarily fill the reduced section of the jig while the rod is being inserted or the blade is being situated so as to temporarily add strength and stability to this section.

Figure 6A:
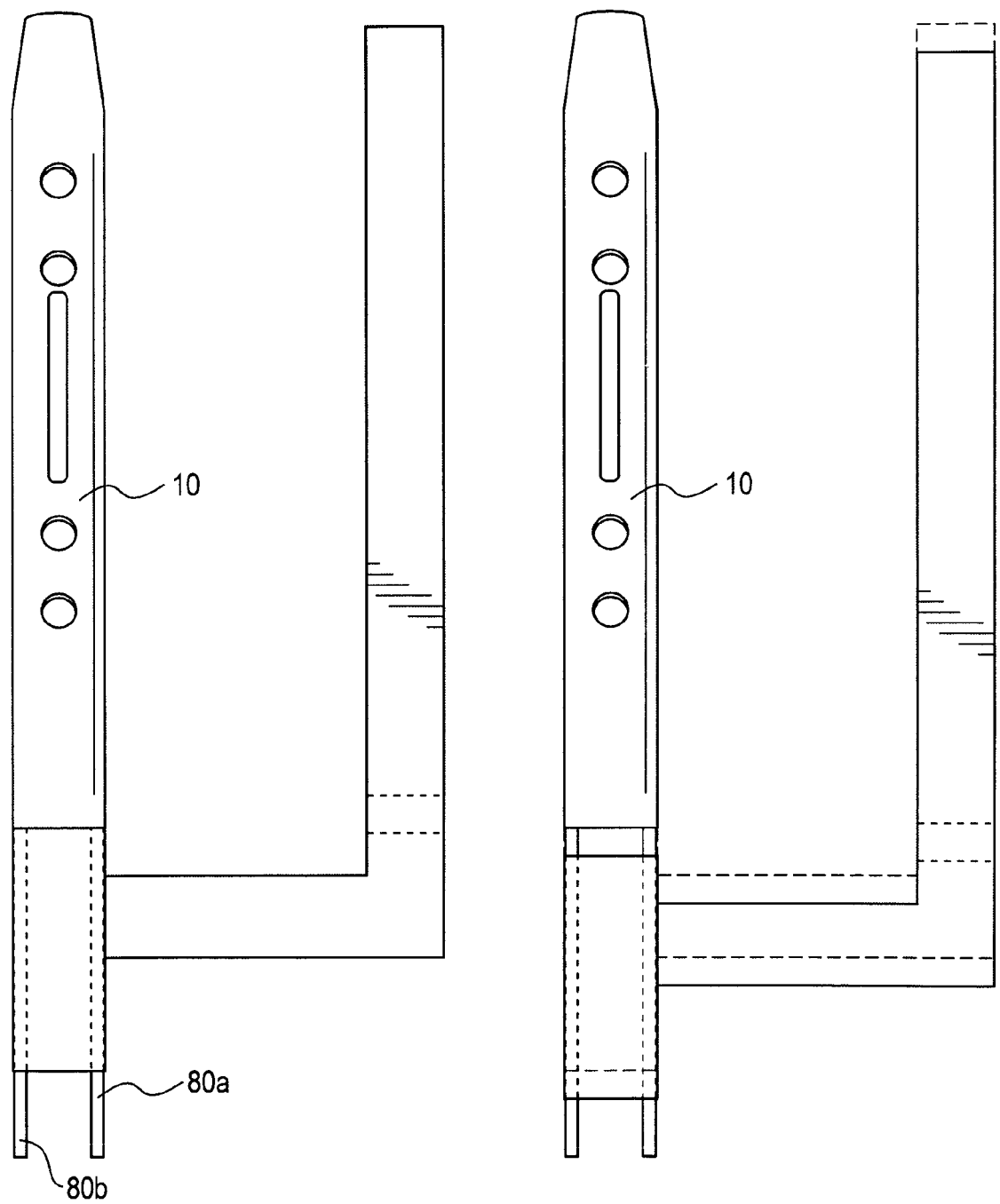
FIGS. 6A-6C illustrate various mechanisms that may be used to back the jig's seat away from the bottom of the rod to allow for insertion of the blade.
Figure 6B:
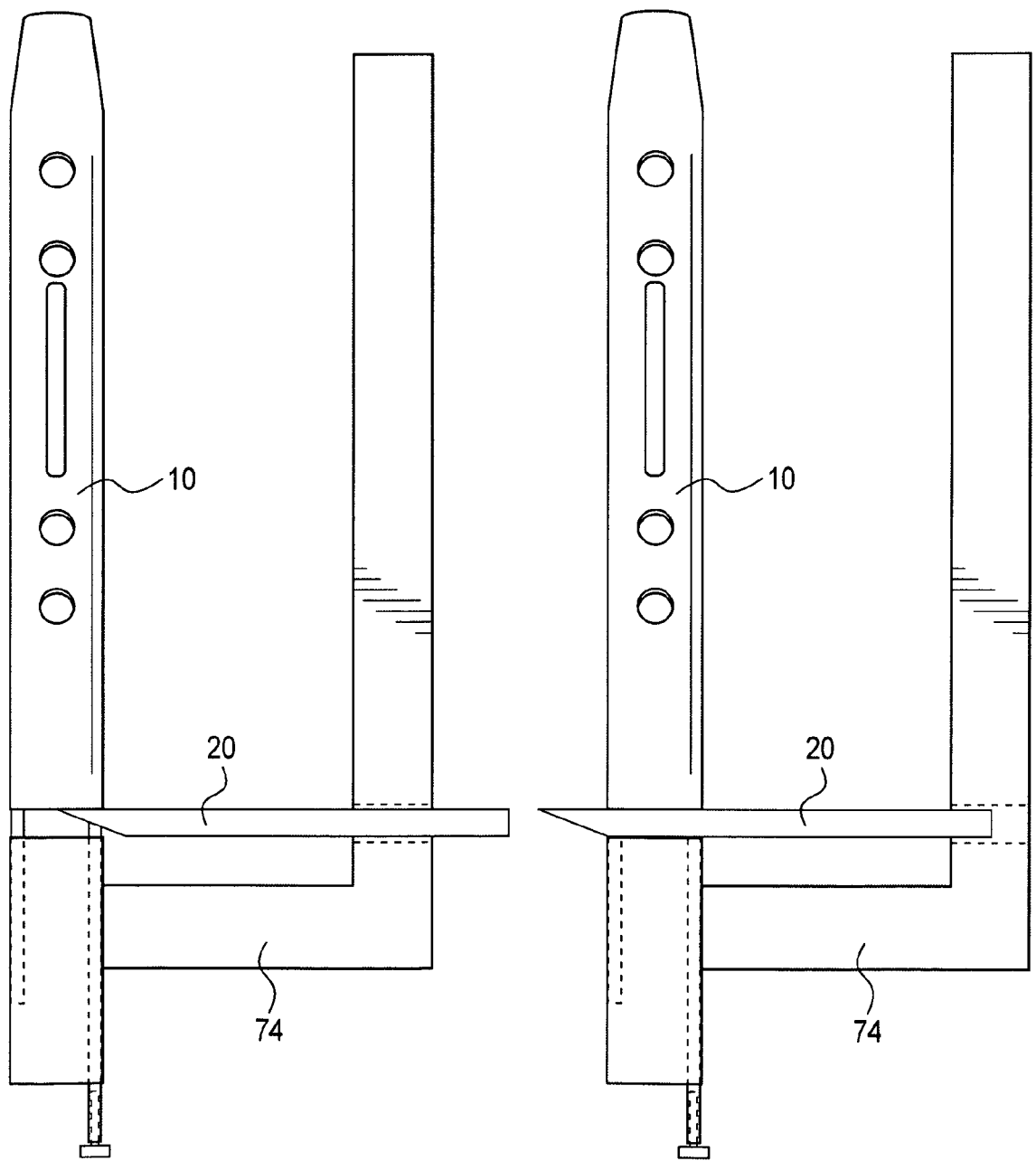
Figure 6C:
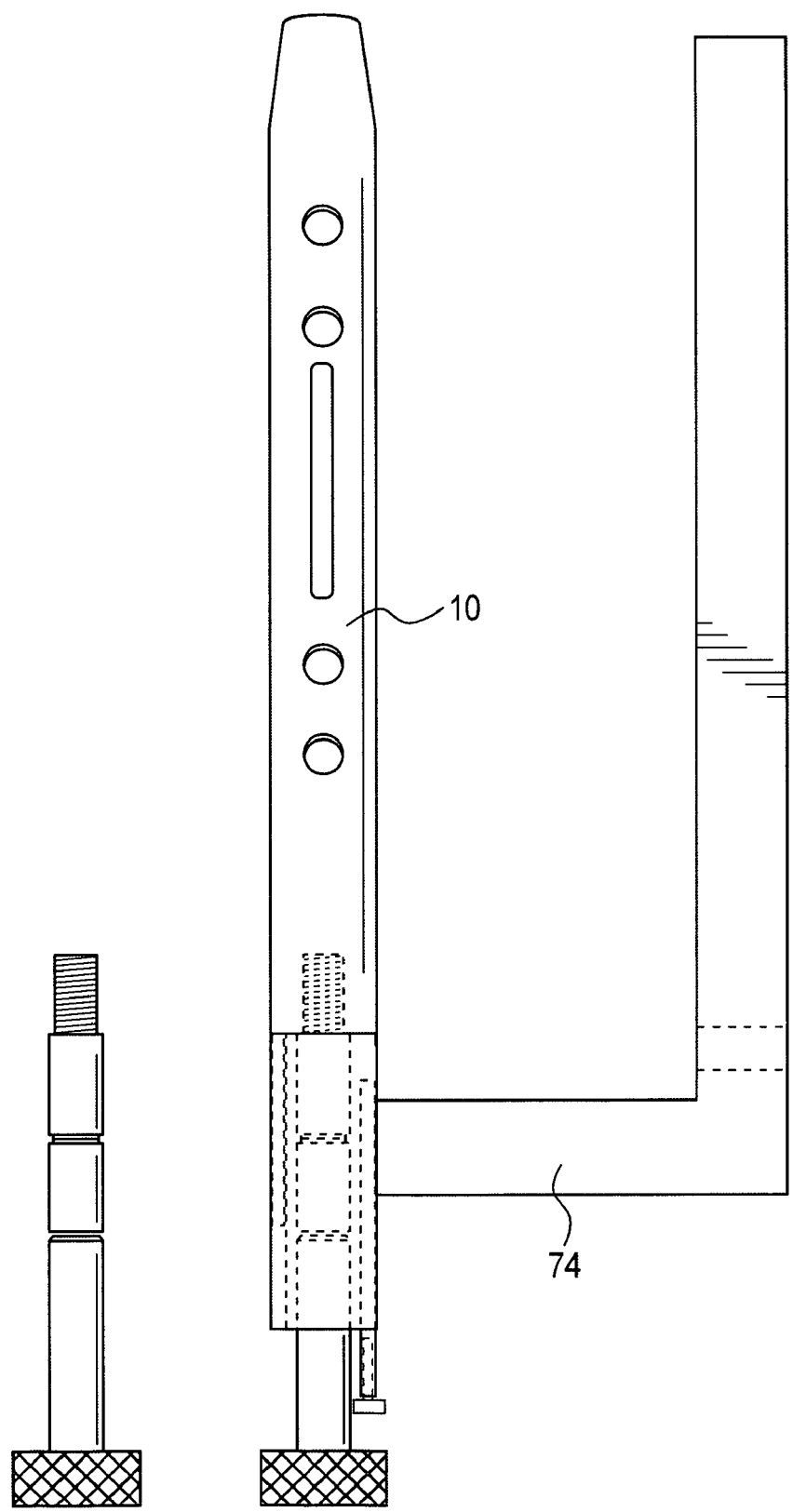

FIGS. 6A-6C illustrate various mechanisms that may be used to back the jig's seat away from the bottom 12 of the rod to allow for insertion of the blade. The left side of FIG. 6A shows the rod's end being flush with the top of the jig's seat portion. Meanwhile, the right hand side of FIG. 6A shows this same hardware after one or more protrusions have been advanced to move the jig's seat portion away from the rod in a controlled fashion thereby allowing passage of the blade through the void that has been created underneath the rod.

Various methods could be used to accomplish this task, including use of bolt/screw jack methods to advance the protrusion against the rod. The protrusion cross-section could be cylindrical; the threaded mechanism(s) could be fused to the cylindrical protrusion or machined as a unit. The protrusion could also be rectangular in cross section, and a screw mechanism used to push directly against the protrusion to advance it against the rod. Use of a thumbnut attached to the jig, and allowed to spin, allows a threaded rod to be used as a screw jack against the rod. Alternatively, with protrusions that are not connected to the jigs' seat but move only in alignment tunnels, the jig could be moved away from the rod by applying a series of downward blows or taps on the jig's seat.

Once the blade is in properly inserted, a cap screw or end cap 50 is used to maintain intimate contact of the blade to the appropriately configured bottom 12 portion of the rod.

Figure 7:
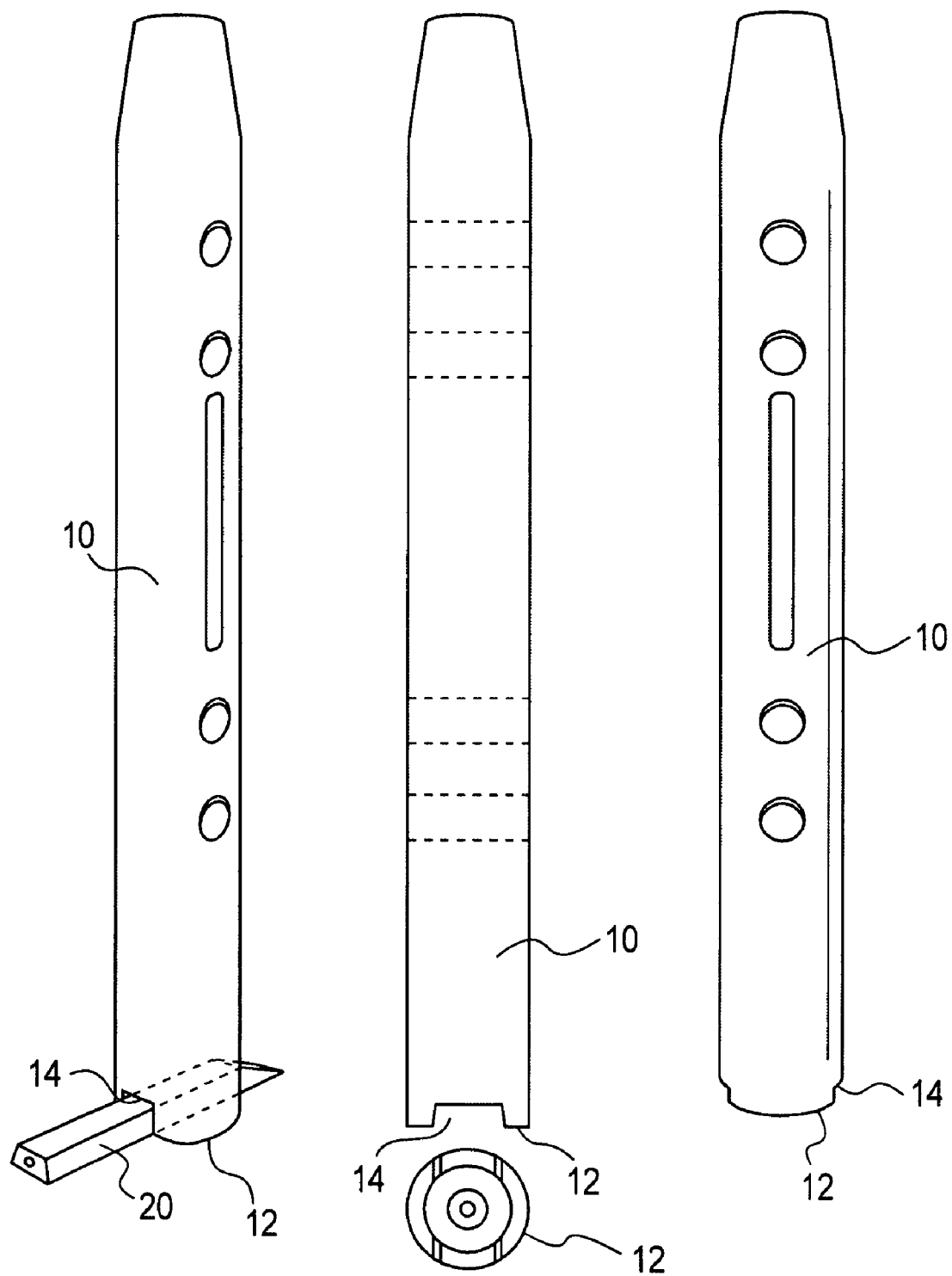
FIG. 7 shows the rod and blade portions for one version of a second preferred embodiment of our improved blade and nail/rod intramedullary fixation device.
Figure 8:
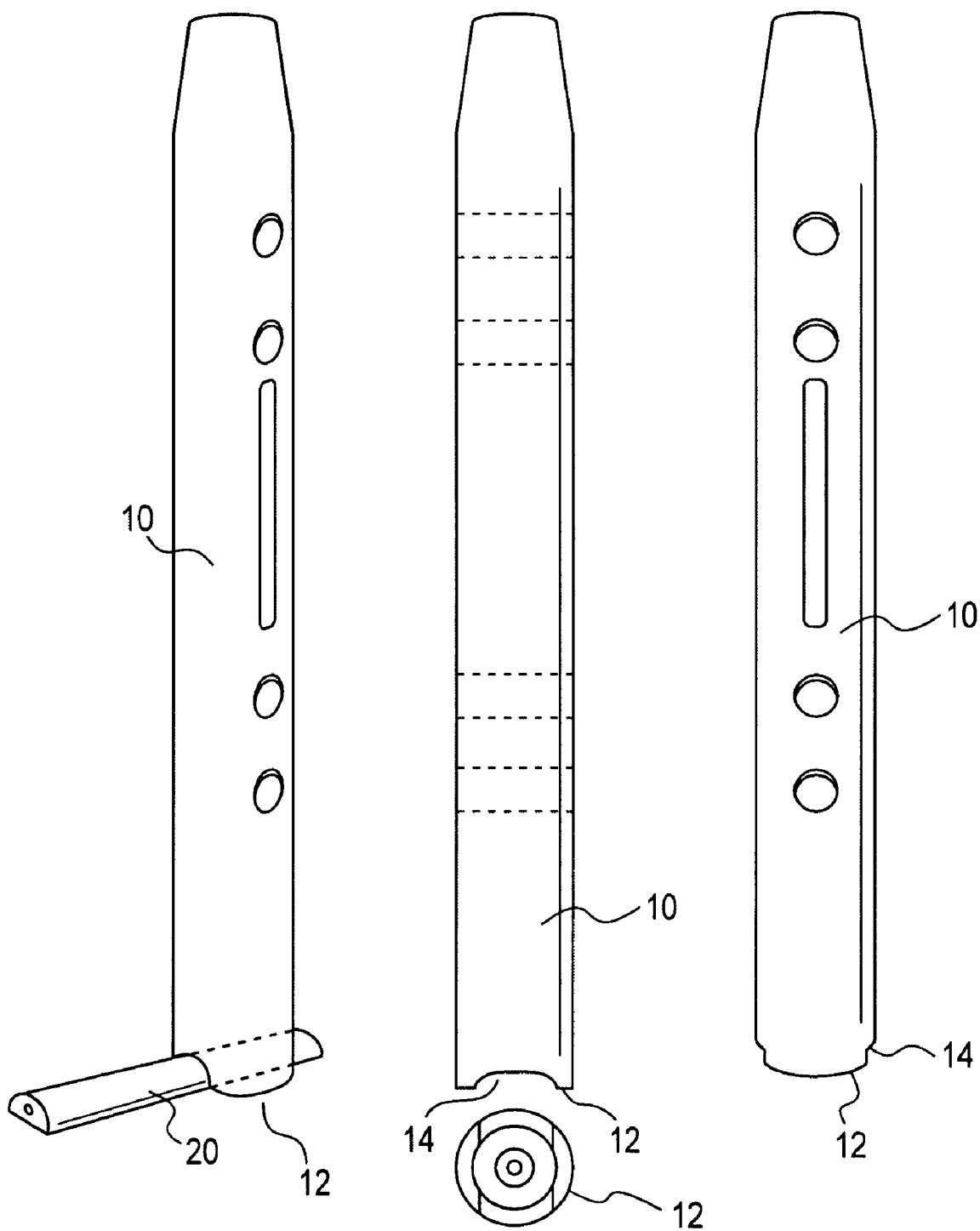
FIG. 8 shows the rod and blade portions for an alternative version of a second preferred embodiment of our improved blade and nail/rod intramedullary fixation device.

FIGS. 7 and 8 show the rod 10 and blade 20 portions for two versions of a second preferred embodiment of our improved blade and nail/rod intramedullary fixation device. In this embodiment, the bottom 12 of the rod has been configured with a channel or recess 14 so as to allow the seating of the blade 20 within said recess without the insertion jig having to be backed away from the rod's bottom. The shape of the recess (e.g., rectangular, tubular, arced, or semi-cylindrical) is dictated by the cross-sectional shape of the to-be-inserted blade. The recess can be partially tapered to allow an interference or locking fit.

Figure 9:
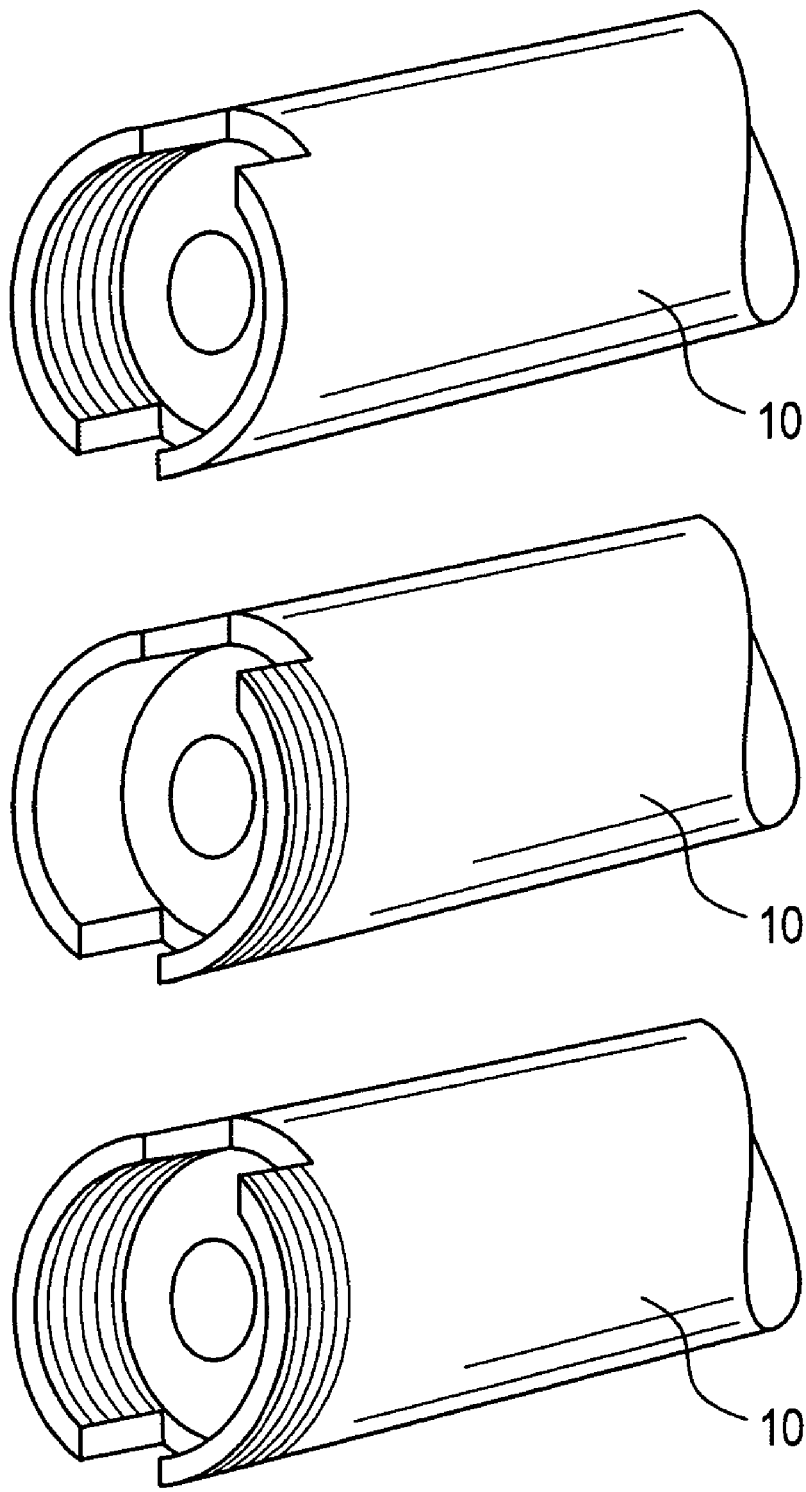
FIG. 9 shows, for this second preferred embodiment, the rod's bottom end and its means of connection to the seat of the insertion jig.

The rod may be connected to the jig with a cannulated screw. The connection point with the jig's seat is enhanced by a ring/shroud of material that partially or completely encases the lower end of the rod and may lock onto the rod with screw threads internally, externally, or both internally and externally. See FIG. 9.

To provide additional stability while inserting the blade, a thin-walled incomplete arc or semi-circular section of a tube may extend from the jig and envelop the rod's bottom end. This extension piece has a section cut out that allows passage of the blade through it.

The recess 14 can be temporarily occluded with a material to protect the void it creates. The occluding material can be penetrable, meltable, or otherwise removable to gain full access to the recess in the rod.

In one version of this second embodiment, the central fixation screw of the jig is positioned below the recess. In another version, this central fixation screw is connected to the jig so as to occlude the recess in order to enhance the rod/jig junction during insertion. After rod insertion, the recess is opened by removing or backing out the central screw leaving the outer shroud connected but not occluding the blade recess.

In yet another version, the outer shroud occludes the recess and is backed off to allow exposure of the blade recess while the central screw maintains the rod/jig junction. Once the blade is in proper position, but before removal of the jig, the external shroud or ring can be used to compress the blade and rod together. In an alternative version, the central screw can be used to apply compression between the blade and rod (while the jig is still attached). In another version, compression may be applied by both the external shroud and the central screw.

Other possible mechanical means for compressing the blade into/against the rod includes an external fixator and/or an impacting device. In yet another version, the jig is removed and compression is achieved by tightening a cap screw. No matter the means of compressing the blade to the rod, an end cap 50 is used to maintain intimate contact of the blade to the rod.

Figure 10:
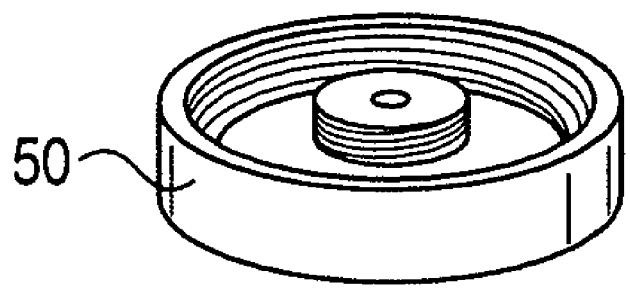
FIG. 10 shows various perspective views of end caps that are suitable for use with rods whose bottom portions have been appropriately configured.
Figure 10:
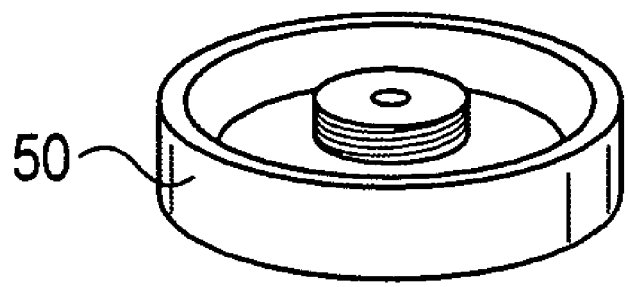
Figure 10:
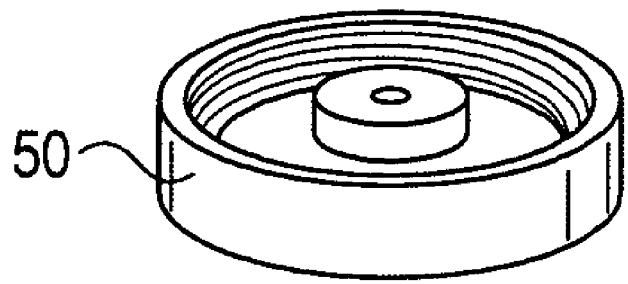
Figure 10:
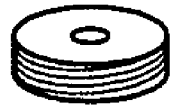

This end cap may have a central protrusion with or without threads; the inner wall of the cap may or may not be threaded. See FIG. 10. The cap mates with the corresponding bottom end of the rod to lock the blade onto the rod. The overall diameter of the cap is larger than the outside of the rod to allow the cap to fit over the rod. At the opposite end of the cap is a hexagonal or other appropriately shaped recess to allow for a means for driving the cap onto the rod.

In a preferred version, this cap is of a one-piece construction. It has a threaded, central protrusion that mates with the corresponding internal threads on the rod. The outer rim of the cap is smooth (no threads) and provides additional bearing surface against the blade.

In another iteration, the internal surface of the cap's rim is threaded so as to mate with corresponding external threads on the rod. In yet another iteration, both the internal surface of the rim and external surface of the protrusion are threaded; these threaded surfaces mate with corresponding threaded surfaces on the rod.

In another preferred version, the cap is composed of two pieces. The first is a central screw that has threads that mate with internal threads on the rod. The second piece is a washer that can rest around the central screw with an outer rim that envelops the outer end of the rod. This outer rim is a bearing surface that compresses the blade into the rod as the screw is tightened.

Figure 11:
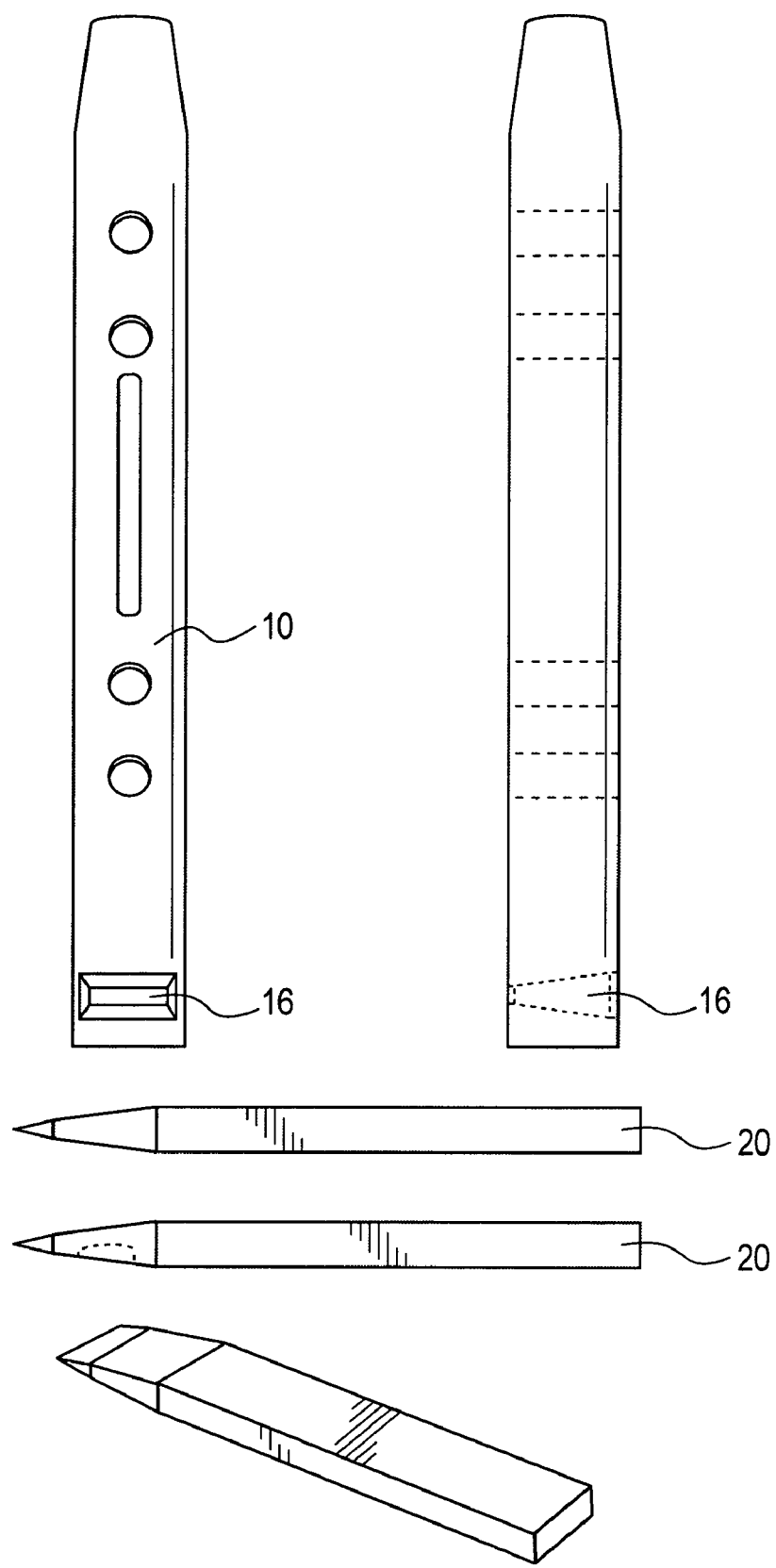
FIG. 11 shows various views of the rod and blade portions of a third preferred embodiment of the present invention.
Figure 12:
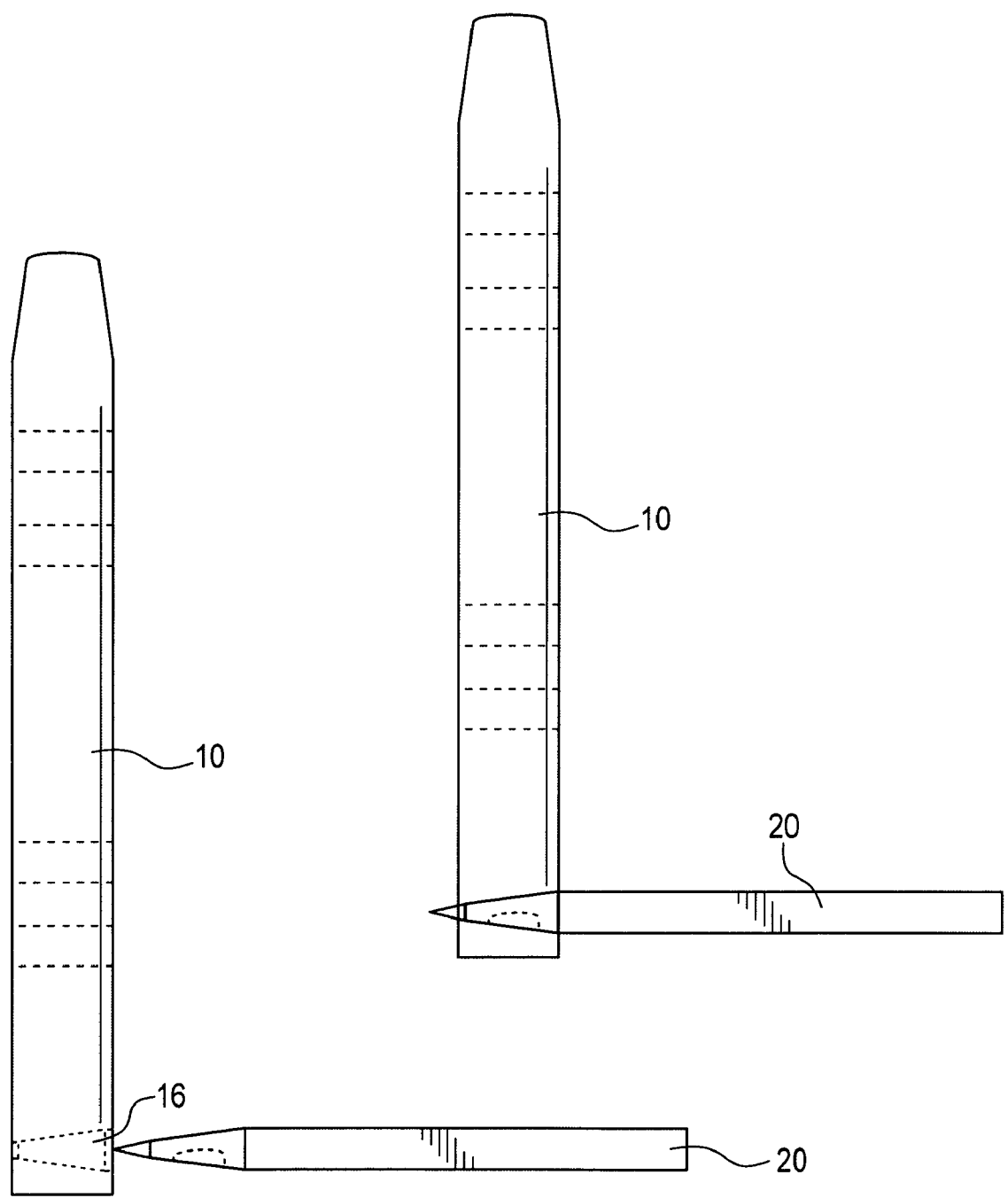
FIG. 12 shows views of the rod and blade portions of FIG. 11 at the beginning of and at the completion of the insertion of the blade into the rod's channel

FIGS. 11 and 12 show the rod 10 and blade 20 portions of a third preferred embodiment of the present invention. This embodiment consists of a rod with an opening or Morse taper shaped channel 16 to accept and interface with a similarly shaped, end portion of the blade. The blade is forced into the channel so as to provide a compression fitting between the parts.

The jig is removed and an end cap or interference screw is inserted to more permanently lock these parts together. The side of the blade that faces the locking screw has a concavity or other recess such that when the locking screw is tightened the blade is further tightened against and/or advanced into the rod. Alternatively the concavity may be neutral.

Although the foregoing disclosure relates to preferred embodiments of the invention, it is understood that these details have been given for the purposes of clarification only. Various changes and modifications of the invention will be apparent, to one having ordinary skill in the art, without departing from the spirit and scope of the present invention.

We claim:

1. An intramedullary fixation device for stabilizing and orienting bones or bone fragments, said device comprising:
   a blade having distal and proximate ends with a longitudinal axis therebetween and a portion between said ends having a specified cross-sectional shape, wherein said cross-sectional shape is configured in consideration of the geometry of a bone into which said blade is to-be-placed and so as to enhance the ability of said blade to stabilize said bone,
   an intramedullary nail having distal and proximate ends, a longitudinal axis extending between said ends, said proximate end terminating in an end cross section that intersects the longitudinal axis of said nail and having a configuration that allows said nail proximate end to be directly attached to and detached from said blade, a coupling element configured so as to interact with said nail so as to lock said nail proximate end directly to said blade and prevent relative movement between said nail and blade, a means for locating and positioning within the bones to-be-treated said nail and said blade and for positioning said nail proximate end with respect to said blade so that said nail proximate end can be directly locked to said blade, and wherein said blade proximate end having a cutting edge and configured so as to enable said blade to be inserted into said bone without requiring said means for locating and positioning to be decoupled from said intramedullary nail proximate end during said blade insertion.

2. An intramedullary fixation device as recited in claim 1, wherein: said blade cross-sectional shape is chosen from the group consisting of an elongated surface with ends and having a protrusion or rail intermediate said ends, an elongated surface having protrusions or rails at the ends of said surface, wherein the cross-sectional shape of said elongated surface may be chosen from the group of shapes consisting of rectangular, tubular, arced or semi-cylindrical, wherein the cross-sectional shape of said protrusions may be chosen from the group of shapes consisting of square, rectangular, circular, triangular, conical, stellar or trapezoidal and wherein said cross-sectional shape between said distal and proximate ends may be chosen from the group consisting of shapes having uniformity in dimensions or a degree of taper over all or a part of the length between said distal and proximate ends.

3. An intramedullary fixation device as recited in claim 1, wherein:

said means for locating and positioning within the bones to-be-treated said nail and said blade and for positioning said nail proximate end with respect to said blade so that said nail proximate end can be directly locked to said blade including an insertion jig having a base, a seat section and a tower section, with said seat section having a seat that is configured to mate with said nail proximate end of said nail and said blade, said blade proximate end having two prongs that are separated by a gap of a specified dimension, said seat having a configuration that is chosen from the group consisting of either having a downsized dimension whose width is such as to allow said downsized seat to fit within said gap of said blade prongs or having a protrusion that extends from said seat with said protrusion having a dimension whose width is such as to allow said protrusion to fit within said gap of said blade prongs.

4. An intramedullary fixation device as recited in claim 3, wherein said protrusion is mobily fixed to said seat in such a manner that said protrusion can be raised a specified height above said seat.

5. An intramedullary fixation device as recited in claim 1, wherein:

said means for locating and positioning within the bones to-be-treated said nail and said blade and for positioning said nail proximate end with respect to said blade so that said nail proximate end can be directly locked to said blade including an insertion jig having a base, a seat section and a tower section, with said seat section having a seat that is configured to mate with said nail proximate end and said blade, and said nail proximate end having a recess that is sized so as to allow said proximate end of said blade to fit within said recess.

6. A method for providing stabilization means for use in fixing the specified, relative position between a tubular bone having a medullary canal and an adjoining bone or section of bone, said method comprising the steps of:

providing an intramedullary nail having distal and proximate ends, a longitudinal axis extending between said ends, said proximate end terminating in an end cross section that intersects the longitudinal axis of said nail and having a configuration that allows said nail proximate end to be directly attached to and detached from said blade, providing a blade having distal and proximate ends with a longitudinal axis therebetween and a portion between said ends having a specified cross-sectional shape, wherein said cross-sectional shape is configured in consideration of the geometry of a bone into which said blade is to-be-placed and so as to enhance the ability of said blade to stabilize said bone, providing a coupling means configured so as to interact with said nail so as to lock said nail proximate end directly to said blade and prevent relative movement between said nail and blade, providing a means for locating and positioning within said tubular bone and said adjoining bone or section of bone said nail and said blade and for positioning said nail proximate end with respect to said blade so that said nail proximate end can be directly locked to said blade, and wherein said blade proximate end having a cutting edge and configured so as to enable said blade to be inserted into said bone without requiring said means for locating and positioning to be decoupled from said intramedullary nail proximate end during said blade insertion.

7. The treatment method as recited in claim 6 wherein the tubular bone is chosen from the group consisting of the tibia, femur or humerus.

* * * * *